United States Patent
Watanabe et al.

(10) Patent No.: US 7,488,529 B2
(45) Date of Patent: Feb. 10, 2009

(54) POROUS FILM AND ITS PRODUCTION PROCESS

(75) Inventors: Kyosuke Watanabe, Shiga (JP); Yasushi Usami, Shiga (JP); Yutaka Kawai, Shiga (JP); Masayoshi Tsujii, Mie (JP)

(73) Assignee: Mitsubishi Plastics, Inc., Tokyo (JP)

( * ) Notice: Subject to any disclaimer, the term of this patent is extended or adjusted under 35 U.S.C. 154(b) by 0 days.

(21) Appl. No.: 10/476,483

(22) PCT Filed: Feb. 8, 2002

(86) PCT No.: PCT/JP02/01094

§ 371 (c)(1),
(2), (4) Date: Nov. 7, 2003

(87) PCT Pub. No.: WO02/090426

PCT Pub. Date: Nov. 14, 2002

(65) Prior Publication Data

US 2004/0170816 A1    Sep. 2, 2004

(30) Foreign Application Priority Data

May 9, 2001  (JP)  ............................. 2001-138122
May 9, 2001  (JP)  ............................. 2001-138125

(51) Int. Cl.
*B32B 5/22* (2006.01)
(52) U.S. Cl. ............... 428/317.9; 428/315.5; 428/315.7
(58) Field of Classification Search ............... 428/317.9, 428/315.5, 315.7; 521/90
See application file for complete search history.

(56) References Cited

U.S. PATENT DOCUMENTS

| 4,331,622 | A | * | 5/1982 | Doi et al. ................... 264/45.3 |
| 4,767,580 | A | * | 8/1988 | Shingo et al. ................ 264/41 |
| 4,791,144 | A | * | 12/1988 | Nagou et al. .................. 521/90 |
| 5,236,963 | A | | 8/1993 | Jacoby et al. |
| 5,595,785 | A | * | 1/1997 | Hindagolla et al. ......... 430/320 |
| 5,922,492 | A | * | 7/1999 | Takita et al. ................ 429/249 |
| 5,945,210 | A | * | 8/1999 | Senba et al. ............. 428/317.9 |
| 6,676,871 | B1 | | 1/2004 | Benassi et al. |

FOREIGN PATENT DOCUMENTS

| GB | 1 534 128 | 11/1978 |
| WO | 00 05295 | 2/2000 |

* cited by examiner

*Primary Examiner*—Hai Vo
(74) *Attorney, Agent, or Firm*—Oblon, Spivak, McClelland, Maier & Neustadt, P.C.

(57) ABSTRACT

It is to provide a porous film which is excellent in gas permeability (air permeability) and moisture permeability (water vapor permeability), and is excellent in anti-leakage properties and anti-bleeding properties against a liquid, hiding properties and masking properties at an adhesion portion, and a process for producing it. A porous film obtained by melting and kneading a resin composition containing a polyolefin resin {component (A)} and a bulking agent {component (B)} as the main components, and a silicone {component (C)}, or a silicone {component (C)} and castor oil {component (D)}, followed by drawing, which shrinks by from 40 to 95% in one direction and expands by from 5 to 40% in a direction transverse thereto, when soaked in a silicone oil of 200 C for 60 seconds, and a process for producing the above porous film, are provided.

20 Claims, No Drawings

POROUS FILM AND ITS PRODUCTION PROCESS

TECHNICAL FIELD

The present invention relates to a porous film and its production process. More particularly, it relates to a porous film which is excellent in gas permeability (air permeability) and moisture permeability (water vapor permeability), which is excellent in anti-leakage properties and anti-bleeding properties against a liquid and hiding properties, and which is excellent also in masking properties at an adhesion portion, and its production process.

The porous film of the present invention is particularly useful for sanitary materials. For sanitary materials, it is useful as back sheets of absorber articles such as disposable diapers, sanitary napkins and hygienic liners. An absorber article basically comprises an absorber which absorbs excretion such as urine or blood, a liquid permeable surface material to be in contact with skin, which covers the surface of said absorber, and a back sheet which covers the above absorber and prevents leak, and they are bonded and integrated.

BACKGROUND ART

Conventionally, many methods for producing a porous film, which comprises drawing a film containing a polyolefin resin and an inorganic bulking agent in a uniaxial or biaxial direction to form pores (voids) connected to each other in the film, have been proposed. Such porous films are used for a variety of applications such as sanitary materials, medical materials, building materials and battery separators.

In recent years, demands for disposable diapers for adults are increasing, and requirements of high gas permeability and moisture permeability have been increasing year by year for back sheets which cover moisture (water) absorptive materials. With respect to diapers for adults, a high pressure is locally applied in the inside thereof, as compared with diapers for children, whereby urine may pass through a gas permeable back sheet and leak out of the diaper, such being problematic. Further, there is an increasing tendency to use gas permeable films for back sheets also in an application of disposable napkins. In the application to napkins, as compared with diapers, a higher pressure is applied, and the surface tension of blood is low as compared with urine, whereby blood is likely to leak through pores as compared with urine.

Further, in recent years, gas permeable films have been used as back sheets for napkins. In such a case, blood absorbed in a moisture (water) absorptive material tends to be seen through the back sheet, and accordingly it has been desired to increase hiding properties of back sheets. Further, when a disposable diaper or napkin is fixed to an underwear by means of an adhesive tape, components contained in the adhesive tape may move to the porous film and make the opaque porous film transparent, whereby the inside may be seen through the film, and such a problem is more severe in a case of napkins.

Accordingly, a porous film which has excellent anti-leakage properties and anti-bleeding properties, which has excellent hiding properties and which has excellent masking properties at an adhesion portion is required. Further, a porous film which does not leak e.g. urine or blood and passes only moisture has been required, in a case where the porous film is used as materials for disposable diapers and sanitary products.

As a means to overcome the above-mentioned problems, a method of blending a bulking agent with a base resin as the main components, and adding at least one member selected from the group consisting of a fatty acid amide, a liquid paraffin and a sorbitan fatty acid ester as an accessory component to obtain a film has been proposed (JP-A-62-250038). According to experiments conducted by the present inventors, uniform drawability without surface irregularity at the time of film production and flexibility of the film to be obtained can be achieved by addition of such an accessory component, but no well balanced film can be obtained in view of anti-bleeding properties against a hydrophilic liquid, gas permeability, moisture permeability and masking properties at an adhesion portion.

Further, JP-A-58-15538 discloses an example wherein liquid polybutadiene, liquid polybutene or terminal hydroxy liquid polybutadiene is added as a hydrocarbon polymer (including one having side chains) as an accessory component. JP-A-58-149925 discloses an example wherein liquid polyisoprene is added. However, according to experiments conducted by the present inventors, it was found that anti-bleeding properties against a hydrophilic liquid are low, drawing tends to be non-uniform, and the hiding properties are low, even if such an accessory component is added.

Further, Japanese Patent No. 1763293 discloses addition of a silicone oil and/or a polyglycerol fatty acid ester surfactant as an accessory component and that addition of such a component increases flexibility, tensile strength, tear strength, uniform drawability, hydraulic pressure resistance and the like of a film. However, according to experiments conducted by the present inventors, it was found that anti-bleeding properties and hiding properties are inadequate with respect to the polyglycerol fatty acid ester. In a case of the silicone oil, good anti-bleeding properties are obtained as compared with the above fatty acid ester or a hydrocarbon polymer, however, it was found that the anti-bleeding properties significantly decrease and the anti-leakage properties are also inadequate, even if the resin composition including the accessory component is the same, unless the orientation state of the film and the pore structure such as pore size and porosity are controlled to be within specific narrow ranges. For example, in a case of a film drawn 3.0 times×3.0 times in a biaxial direction, the orientation state of the film tends to be isotropic, whereby not only permeability of a liquid in a thickness direction tends to be too high, but also the anti-bleeding properties are inadequate since the pore size is too large.

DISCLOSURE OF THE INVENTION

Under these circiumstances, the present inventors have conducted extensive studies with the purpose of obtaining a porous film which is excellent in gas permeability and moisture permeability, which has excellent anti-leakage properties and anti-bleeding properties against a liquid and good hiding properties, and which has good masking properties at an adhesion portion, and a process for producing it, and as a result, have accomplished the present invention.

The present invention provides a porous film obtained by melting and kneading a resin composition containing a polyolefin resin {component (A)} and a bulking agent {component (B)} as the main components, and a silicone {component (C)}, or a silicone {component (C)} and castor oil {component (D)}, followed by drawing, which shrinks by from 40 to 95% in one direction and expands by from 5 to 40% in a direction transverse thereto, when soaked in a silicone oil of 200° C. for 60seconds.

The present invention further provides a process for producing a porous film, which comprises melting and kneading a resin composition containing a polyolefin resin {component (A)} and a bulking agent {component (B)}as the main components, and a silicone {component (C)}, or a silicone {component (C)} and castor oil {component (D)}, into a film, and drawing the obtained film from 1.2 to 5 times only in a uniaxial direction at a temperature of from 23° C. to the softening temperature of the resin (as measured in accordance with JIS K6760).

BEST MODE FOR CARRYING OUT THE INVENTION

Now, the present invention will be explained in detail below.

The porous film of the present invention is produced from a resin composition comprising a polyolefin resin (hereinafter sometimes referred to simply as component (A)) as a base. In the present invention, the polyolefin resin is one containing a polymer or a copolymer of a monoolefin such as ethylene, propylene or butene as the main component. Specifically, it may, for example, be a high density polyethylene, a branched low density polyethylene, a linear low density polyethylene, polypropylene, an ethylene-propylene random copolymer, an ethylene/propylene block copolymer, polybutene, an ethylene/vinyl acetate copolymer or a mixture thereof. Among them, particularly preferred for sanitary materials is a linear low density polyethylene since it is flexible and tough.

The linear low density polyethylene is preferably mixed with a branched low density polyethylene. The linear low density polyethylene is a copolymer of ethylene with an α-olefin having a carbon number of from 3 to 8 as its molecular skeleton. Preferred as the linear low density polyethylene is one having a density of from 0.890 to 0.950 g/cm³ and a melt index (MI) of from 0.1 to 8 g/10 min.

In the present invention, the density is a value as measured in accordance with JIS K7112, and the melt index (MI) is a value as measured in accordance with JIS K7210. If the density is less than 0.890 g/cm³, the uniform drawability tends to decrease at the time of producing a film, and if it exceeds 0.950 g/cm³, the softness of the drawn film tends to be impaired. Further, if the melt index is less than 0.1 g/10 min, abnormal flow tends to take place at the time of producing a film, whereby no film having a uniform thickness tends to be produced, and if it exceeds 8 g/10 min, the uniform drawability tends to be impaired.

The branched low density polyethylene is obtained by polymerizing ethylene by a conventionally known high pressure method, and has a melt index of from 0.1 to 8g/10 min and a density of from 0.900 to 0.930 g/cm³. If the melt index is less than 0.1 g/10 min, the branched low density polyethylene tends to hardly be mixed with the linear low density polyethylene, and if it exceeds 8g/10 min, no film having a uniform thickness tends to be obtained. Further, if the density exceeds 0.930, it tends to be difficult to produce a film having a uniform thickness.

In a case where the linear low density polyethylene is used as a mixture with the branched low density polyethylene, it is preferred to combine them in a proportion of from 30 to 98 wt % of the linear low density polyethylene and from 2 to 70 wt % of the branched low density polyethylene. If the branched low density polyethylene exceeds 30 wt %, film may not extend in a molten state, and it tends to be difficult to form a film, and if it is less than 2 wt %, it tends to be difficult to obtain a film having a uniform thickness. Within the above range, particularly preferred is a mixture comprising from 70 to 96 wt % of the linear low density polyethylene and from 4 to 30 wt % of the branched low density polyethylene.

With the polyolefin type resin, for the purpose of imparting flexibility to the film, an ionomer such as an ethylene-ethyl acrylate copolymer, an ethylene-methyl acrylate copolymer, an ethylene acrylate copolymer or an ethylene-methacrylate copolymer, an olefin type elastomer such as ethylene-propylene rubber (EPR), ethylene-butylene rubber (EBM) or an ethylene-propylene-diene terpolymer (EPDM) or an ethylene/vinyl alcohol copolymer may further be mixed.

With the component (A), an inorganic or organic bulking agent {hereinafter sometimes referred to simply as component (B)} may be blended as the main components. The component (B) imparts moisture permeability by forming pores in the film to make it porous at the time of producing a film from the resin composition, and prevents bleeding of urine or blood. Specific examples of the inorganic bulking agent as the component (B) include calcium carbonate, barium sulfate, calcium sulfate, barium carbonate, magnesium hydroxide, aluminum hydroxide, zinc oxide, magnesium oxide, titanium oxide, silica and talc. Specific examples of the organic bulking agent include cellulose powders such as wood flour and pulp flour. Among them, particularly preferred are calcium carbonate and barium sulfate.

The average particle size of the component (B) has a great impact on the anti-bleeding properties, and the average particle size is within a range of from 0.5 to 3.0 μm. If the average particle size is less than 0.5 μm, pores are hardly formed on the film, and the gas permeability and the moisture permeability tend to be inadequate, and if it is larger than 3.0 μm, the pores tend to be too large, and the bleeding amount of urine or blood tends to be large. The component (B) is preferably one having a surface treatment applied thereto in order to improve dispersibility with the component (A). The surface treating agent is not particularly limited, but is preferably one which covers the surface of the component (B) to prevent agglomeration and to make the surface hydrophobic. It may, for example, be a higher fatty acid such as stearic acid or lauric acid, or a metal salt thereof. Here, the average particle size of the component (B) means a value calculated from the specific surface area as measured by a constant pressure transmission method (measured by means of Shimadzu type powder specific surface area measuring apparatus, model: SS-100).

The resin composition of the present invention contains the above components (A) and (B) as the main components, and further contains a silicone (hereinafter sometimes referred to simply as component (C)), or the component (C) and castor oil (hereinafter sometimes referred to simply as component (D)). The component (C), or the components (C) and (D) improve processability when a porous film is produced, improves water repellency of the porous film, and imparts to the porous film adhesive properties with an adhesive tape and good anti-bleeding properties and masking properties. The silicone component (C) is a silane monomer (C1) and/or silicone (C2) having a siloxane bond as a skeleton, and the silane monomer (C1) may be a compound represented by the following general formula [I]:

$$R_a\text{—}SiX_{4-a} \qquad [I]$$

wherein a is an integer of from 0 to 3, R is H or an organic group such as $CH_3$, $C_6H_6$ or $C_nH_{2n+1}$ (including a hydrolyzable group), and X is a hydrolyzable group such as Cl, $OCH_3$ or $OC_2H_5$.

Specifically, the compound of the general formula [I] wherein X is an alkoxy group may, for example, be an ethoxysilane such as methyltriethoxysilane, dimethyldiethoxysilane, tetraethoxysilane, phenyltriethylsilane, diphenyldiethoxysilane or hexyltriethoxysilane, or a methoxysilane such as tetramethoxysilane, methyltrimethoxysilane, dimethyldimethoxysilane, phenyltrimethoxysilane, diphenyldimethoxysilane, hexyltrimethoxysilane, decyltrimethoxysilane or vinyltrimethoxysilane.

An organohalosilane of the above formula [I] wherein X is e.g. a chloro group may be methyltrichlorosilane, dimethyldichlorosilane, trimethylchlorosilane, methyldichlorosilane, phenyltrichlorosilane, diphenyldichlorosilane, vinyltrichlorosilane or vinylmethyldichlorosilane. Further, a halogenated silane may, for example, be monosilane, disilane, trichlorosilane, dichlorosilane or tetrachlorosilane, one having an amide linkage in its molecule may, for example, be hexamethyldisilazane, N,O-bis(trimethylsilyl)acetamide or bis(trimethylsilyl)urea, and one having a fluorine atom in its molecular may, for example, be trifluoropropyl trimethoxysilane, heptadecatrifluorodecyl trimethoxysilane or trifluoropropyl trichlorosilane. Particularly preferred is an alkoxysilane to impart high anti-leakage properties to the film.

The silicone (C2) may, for example, be a silicone oil, a silicone rubber or a silicone resin. The silicone oil may, for example, be one consisting of siloxane bonds and alkyl groups alone such as dimethyl polysiloxane (dimethylsilicone oil), polymethylphenylsiloxane or cyclic dimethyl polysiloxane, or one having alkyl groups modified by various functional groups such as an epoxy modified silicone oil, an amino modified silicone oil, a polyether modified silicone oil, a carboxyl modified silicone oil, an alcohol modified silicone oil, a methacryl modified silicone oil, a methylstyryl silicone oil, a fluorine modified silicone oil, a mercapto silicone oil, a methylstyryl modified silicone oil, a higher fatty acid modified oil or a methylalkoxy modified silicone oil.

Further, as the silicone resin, in addition to conventional dimethylpolysiloxane, a polymer of trimethylsiloxysilicic acid may, for example, be mentioned. Further, as a gummy silicone rubber, a heat crosslinkable (HTV) millable rubber, a liquid rubber or a room temperature curable (RTV) liquid rubber may, for example, be mentioned. Further, a copolymer of monomers having a siloxane-siloxane structure such as a dimethylsiloxane/methylstearoxysiloxane copolymer or a modified silicone rubber (SEP) obtained by modifying an ethylene/propylene rubber by a special polyorganosiloxane may, for example, be mentioned.

The castor oil component (D) in the present invention is a derivative obtained by operations such as purification, dehydration and hydrogenation from a natural non-drying oil obtained from castor seed. It may, for example, be a castor oil which is a liquid at room temperature such as purified castor oil, dehydrated castor oil, polymerization dehydrated castor oil or a suction castor oil, or a castor oil which is a solid at room temperature such as hardened castor oil. Among them, preferred is a hardened castor oil. As compared with a fatty acid monoester or polyester such as fatty acid glyceride synthesized by e.g. dehydration polymerization, the castor oil which is prepared from a natural compound, has lower affinity with another oil and general organic solvents with some exceptions, due to influence of the hydrogen bond in a functional group such as a hydroxyl group in its molecule or due to a crystal structure resulting from the hydrogen bond. When such a nature is combined with a silicone (C2) having a siloxane bond as a skeleton, better adhesive properties and masking properties, more excellent anti-bleeding properties and the like are obtained.

The resin composition for production of the porous film preferably contains from 25 to 50 parts by weight of the component (A) and from 75 to 50 parts by weight of the component (B), and from 0.1 to 10 parts by weight of the component (C) based on 100 parts by weight of the two components (A) and (B). When the components (A) and (B) are combined, if the component (B) is less than 50 parts by weight, pores (voids) adjacent to one another, formed by separation of an interface between the components (A) and (B), are not connected with one another, whereby no preferred gas permeability tends to be obtained. Further, if the component (B) exceeds 75 parts by weight, the film may not extend at the time of drawing, whereby drawing tends to be difficult.

The silicone {component (C)} shows a low affinity to general solvents, and when this nature is combined with the silane monomer (C1) and/or the silicone (C2) having a siloxane bond as a skeleton, more preferred adhesive properties and masking properties, more excellent anti-bleeding properties and the like are obtained.

The component (C) is constituted by the silane monomer (C1) and/or the silicone (C2) as mentioned above. The addition amount of the component (C) has impact on drawability at the time of film production, uniformity in thickness, texture, post-processability, moisture resistance, hydrophilicity, anti-bleeding properties against a liquid, adhesive properties with an adhesive tape, hiding properties, etc. If the addition amount of the component (C) is too large, the above component moves from the porous film to an adhesive layer or a tackifier layer, whereby the adhesive strength tends to decrease, the porous film tends to be transparent, and the masking properties tend to decrease. If the addition amount of the component (C) is too small, water repellency on the surface of the porous film tends to decrease, whereby no adequate anti-bleeding effect against a hydrophilic liquid can be obtained, and further, flexibility of the porous film tends to be impaired, the transparency of the porous film tends to be too good, and when the film is used for e.g. a back sheet for napkins, blood absorbed in a moisture (water) absorptive material may be seen through the back sheet, such being unfavorable.

Taking the above circumstances, into consideration, the addition amount of the component (C) is preferably within the above range. If it is less than 0.1 part by weight based on 100 parts by weight of the two components (A) and (B), no adequate anti-bleeding properties and masking properties may be imparted to the porous film produced from the resin composition, and if it exceeds 10parts by weight, productivity of the porous film tends to decrease. It is particularly preferably from 0.5 to 5parts by weight.

The resin composition for production of the porous film contains at least the above three components (A), (B) and (C), and may further contain the castor oil component (D). By addition of the castor oil (D), further improvement in adhesive strength and masking properties can be expected.

Taking the above circumstances into consideration, the addition amount of a mixture component (E) of the components (C) and (D) is preferably within the above range. If it less than 0.1 part by weight based on 100parts by weight of the two components (A) and (B), no adequate anti-bleeding properties and masking properties may be imparted to the porous film produced from the resin composition, and if it exceeds 10 parts by weight, productivity of the porous film tends to decrease. It is particularly preferably from 0.5 to 5 parts by weight.

The proportion of the castor oil {component (D)} to the silicone component (C) consisting of a silane monomer and/or a silicone having a siloxane bond as a skeleton, constituting the component (E), is preferably such that (D)/(C) is from 0 to 1.0 as a weight ratio. When the total amount of the components (D) and (C) is the same, if the proportion of the castor oil (D) is low, adhesive properties and masking properties tend to be inadequate due to movement to an adhesive layer or a tackifier layer, and if the proportion is too high, anti-bleeding properties and hiding properties of the porous film tend to decrease.

The resin composition for production of the porous film contains the above components (A) and (B) as the main components, and contains the component (C) or the components (C) and (D), and in addition to them, it may contain conventionally known various resin additives such as a processing aid {hereinafter sometimes referred to simply as component (F)}, an antioxidant, a heat stabilizer, a photostabilizer, an ultraviolet absorber, a neutralizing agent, an anti-fogging agent, an anti-blocking agent, an antistatic agent, a slipping agent and a coloring agent. The blending amount of such resin additives is preferably at most 5 parts by weight based on 100 parts by weight of the above resin composition, and they may be used alone or in combination.

The processing aid {component (F)} may, for example, be an amide compound, a hydrocarbon compound having side chains, a mineral oil or wax. The amide compound is not particularly limited so long as it is a mono- or polyamide compound comprising an amine and a carboxylic acid, and it may be either a compound having amino group and carbonyl group terminals left in its molecule or a compound having them sealed in a form of an amide group. Specifically, it may, for example, be stearic acid amide, behenic acid amide, hexamethylene bisstearic acid amide, trimethylene bisoctylic acid amide, hexamethylene bishydroxystearic acid amide, trioctatrimellitic acid amide, distearyl urea, butylene bisstearyl acid amide, xylylene bisstearic acid amide, distearyladipic acid amide, distearylphthalic acid amide, distearyloctadecanedioic acid amide, ε-caprolactam or a derivative thereof.

The hydrocarbon polymer having side chains is preferably a poly α-olefin classified into a normal oligomer having side chains with a carbon number of at least 4. Specifically, it may, for example, be an ethylene/propylene copolymer or its maleic acid derivative (such as LUCANT, tradename, manufactured by Mitsui Petrochemical Industries, Ltd.), a polymer of isobutylene (such as Polybutene HV-100, tradename, manufactured by Idemitsu Petrochemical Co., Ltd.), an oligomer of butadiene or isoprene or its hydrate, a polymer of 1-hexene, a polymer of polystyrene or a derivative derived therefrom, hydroxypolybutadiene or its hydride, or terminal hydroxy polybutadiene hydride (Polytel HA, tradename, manufactured by Mitsubishi Chemical Corporation). The mineral oil may, for example, be liquid paraffin or paraffin wax.

To prepare the resin composition for production of the porous film, either of the following methods may be employed. (1) Firstly, the above components (A), (B) and (C), or the components (A), (B), (C) and (D), and another resin additive as the case requires, are respectively weighed, and the respective components are mixed by a mixture such as a drum tumbler, a ribbon blender, a Henschel mixer or a super mixer to obtain a mixture, followed by melting and kneading by means of a kneading machine such as a uniaxial extruder, a biaxial extruder, mixing rolls or a Banbury mixer for pelletizing.

(2) The components (A) and (C) or the components (A), (C) and (D) are preliminarily mixed, and the component (B) and another resin additive as the case requires are mixed therewith and kneaded. Here, the porous film of the present invention may be directly produced from the mixture without pelletizing the mixture of the respective components.

To produce the porous film from the above resin composition, the pellets or the mixture prepared by the above method is melted and kneaded by an extruder to form a film. To form a film, a non-drawn film is produced by a conventionally known method such as inflation method or T-die method, and then the film is drawn only in one direction i.e. longitudinal direction (film drawing direction, MD) to obtain a drawn film. The draw ratio is preferably from 1.2 to 5.0 times. Here, in the present invention, a film which slightly extends in a lateral direction (direction transverse to the film drawing direction, TD) when drawn only in MD direction is not excluded.

To draw the non-drawn film, a conventionally known method such as a roll method, a tenter method or a tubular method may be employed. For drawing, drawing is carried out at least in a uniaxial direction at a temperature of from 23° C. to the softening point of the component (A) (as measured in accordance with JIS K6760) to separate the interface between the components (A) and (B) in the film to obtain a porous film. If the temperature is lower than 23° C., the pore size tends to be too large. The drawing may be either one step (simultaneous) drawing or multi step of at least two steps (sequential) drawing.

The thickness of the porous film is not particularly limited, but is preferably from 10 to 200 μm. If the thickness is less than 10 μm, the strength of the porous film tends to be inadequate, whereby the film is likely to fracture at the time of post-processing, and if it exceeds 200 μm, the porous film tends to be hard, whereby no film having softness and texture like those of cloth can be obtained.

The porous film preferably has a maximum pore size of pores of from 0.05 to 0.3 μm. The pores have such a function that when the porous film is used as a back sheet for diapers, the porous film does not leak a liquid absorbed in a moisture (water) absorptive material out of the diaper and transmits moisture alone. The pores are formed by separation of the interface between the components (A) and (B) by drawing the non-drawn film.

The porous film preferably has a porosity of from 10 to 40%. If the porosity is less than 10%, the gas permeability and moisture permeability of the porous film tend to be inadequate, and if it exceeds 40%, hydrophilicity and anti-bleeding properties against a liquid tend to be inadequate.

The porous film preferably has a windability W of from 0.4 to 4.0. The windability W is an index of connectivity of pores in a thickness direction, indicating how the flow path bends, on the assumption that the pores in the porous film are tubular. A small value means a short flow path length in a thickness direction, and a great value means a long flow path length. The windability W is calculated from the following formula:

Windability $W$ (sec/100 cc)={gas permeability (sec/100 cc)×porosity×peak pore size (μm)}/film thickness (μm)

If the windability W is less than 0.4, the flow path length in a thickness direction tends to be short, whereby urine or blood is likely to leak, and if it exceeds 4.0, gas permeability and moisture permeability significantly decrease, and accordingly when the porous film is applied to e.g. disposable napkins, the skin is likely to be smothered.

The orientation state of the porous film can be evaluated by the shrinkage percentage when the porous film is soaked in a silicone oil of 200° C. for 60 seconds. It is very important to control the orientation state of the pores in order to obtain all the properties of anti-bleeding properties against fluid such as urine or blood, moisture permeability (water vapor permeability) and gas permeability (air permeability).

It is required that the porous film has a shrinkage percentage of from 40 to 95% in one direction when soaked in a silicone oil of 200° C. for 60 seconds and at the same time, it extends from 5 to 40% in a direction transverse thereto. Usually the direction of shrinkage is the MD direction in which the draw ratio is high, and the direction transverse thereto is the TD direction in which the draw ratio is low. When the shrinkage percentage is within the above range under the above heating conditions, both anti-bleeding properties and moisture permeability or gas permeability tend to be good.

Of the porous film, the maximum pore size of pores, porosity, heat shrinkage percentage, thickness, windability W, etc. can easily be controlled by selecting the type and the blending ratio of the component (A), the type, the average particle size and the blending ratio of the component (B), the type and the blending ratio of the component (C), the type and the blending ratio of the component (D), temperature conditions at the time of film production, the draw ratio and the drawing temperature.

The porous film of the present invention has moderate gas permeability, moisture permeability, masking properties regarding movement of adhesive components, good anti-bleeding properties, hiding properties and flexibility. Accordingly, it is very useful for sanitary materials such as disposable diapers, fluid-absorbing pads and bed sheets, medical materials such as surgical coats and substrates for poultice, clothing materials such as jackets and rain apparel, building materials such as wall paper and roof waterproof materials, drying agents, moistureproof agents, deoxidizers, disposal body warmers, packaging materials for e.g. freshness-keeping packaging and food packaging and industrial materials such as separators for batteries.

EXAMPLES

Now, the present invention will be explained in further detail with reference to Examples. However, it should be understood that the present invention is by no means restricted to such specific Examples.

Examples 1 to 15

Components used in the following Examples, as identified in Tables 1 and 2 by symbols, are as follows.
(1) 20G: Component (A), linear low density polyethylene having a density of 0.921 g/cm$^3$ and MI of 1 g/10 min (FW20G, tradename, manufactured by Japan Polychem Corp.).
(2) 441: Component (A), branched low density polyethylene having a density of 0.919 g/cm$^3$ and MI of 2g/10 min (LF441, tradename, manufactured by Japan Polychem Corp.).
(3) NS#1000: Component (B), obtained by subjecting 100parts by weight of calcium carbonate having an average particle size of 1.2 μm (NS#1000, tradename, manufactured by NITTO FUNKA KOGYO K.K.) to a surface treatment with 2parts by weight of stearic acid.
(4) Softon 2600: Component (B), obtained by subjecting 100 parts by weight of calcium carbonate having an average particle size of 0.9 μm (Softon 2600, tradename, manufactured by BIHOKU FUNKA KOGYO K.K.) to a surface treatment with 2 parts by weight of stearic acid.
(5) BF100: Component (B), obtained by subjecting 100parts by weight of calcium carbonate having an average particle size of 3.6 μm (Softon 2600, tradename, manufactured by BIHOKU FUNKA KOGYO K.K.) to a surface treatment with 2 parts by weight of stearic acid.
(6) A: Silicone monomer as the component (C), hexyltrimethoxysilane (KBM3063, tradename, manufactured by Shin-Etsu Silicone K.K.).
(7) B: Silicone oil as the component (C) {dimethylsilicone L45(5000), tradename, manufactured by UNICAR CO., LTD.}.
(8) C: Silicone monomer as the component (C) (silane monomer A-162, tradename, manufactured by UNICAR CO., LTD.).
(9) D: Terminal hydroxypolybutadiene as the component (F) (Polytel HA, tradename, manufactured by Mitsubishi Chemical Corporation).
(10) E: Glycerol mono-diricinoleate as the component (F) (RIKEMAL R-200, tradename, manufactured by Riken Vitamin Co., Ltd.).
(11) F: Tetraglycerol stearate as the component (F) (POEM J-4081, tradename, manufactured by Riken Vitamin Co., Ltd.).
(12) G: Hexamethylenebisstearic acid amide as the component (F) (hexamethylenebisstearic acid amide ZHS, tradename, manufactured by Nippon Kasei Chemical Co., Ltd.).

In the following Examples, various physical properties were evaluated by the following methods.
(a) Average particle size (μm): With respect to the component (B), it was calculated from the specific surface area as measured by a constant pressure transmission method (by using Shimadzu type powder specific surface area measuring apparatus SS-100). Measurement was carried out under such conditions that the weight of the sample was 3.0 g, the thickness of the sample was 1.35 cm, the cross-sectional area of the sample layer was 2 cm$^2$, and the air pressure was 50 cm H$_2$O, and calculation was carried out assuming that the coefficient of viscosity of the air was $181 \times 10^{-6}$ g/(cm.sec).
(b) Shrinkage percentage (%): Using a sample porous film, a line was drawn on the film to indicate a direction, the film was punched into a disc having a diameter of 10 mm and soaked in a silicone oil having its temperature adjusted to 200° C., and a maximum (MAX) shrinkage percentage and a minimum (MIN) shrinkage percentage (expansion coefficient) were measured. The signal minus (−) represents expansion coefficient.
(c) Maximum pore size, peak pore size (μm): It was measured in accordance with JIS K3832 by using a porometer manufactured by Coulter. The maximum pore size is, in the measured pore size distribution, a pore size at a point at which the distribution curve arises from the pore number=0 at the end of the larger pore size side. The peak pore size is a pore size at a portion at which the number of pores per unit area is greatest in the measured pore size distribution, and approximates to the average pore size in the case of the porous film.
(d) Porosity (%): A sample of 10 cm square was cut out from the sample porous film, its weight w (g) and thickness t (mm) were measured, and the porosity was calculated from the specific gravity ρ (g/cm$^3$) of the resin composition from the following formula:

$$\text{Porosity }(\%)=[1-\{w/(10\times10\times t\times0.0001\times\rho)\}]\times100$$

(e) Windability: It was calculated from the following formula {gas permeability (sec/100 cc)×porosity (−)×peak pore size (μm)}/thickness (μm) of the porous film.
(f) Gas permeability (sec/50 cc): It was measured in accordance with JIS P8117. With respect to the gas permeability, the smaller the value, the easier the gas passes through the film, and it is preferably from 100 to 2,000 sec/50 cc.

(g) Bleeding test (g): A cotton was put on the sample porous film, 3 cc of a test liquid (0.01 wt % aqueous solution of Aerosol-OT) was dropped thereon, a weight having a diameter of 60 mm and a weight of 2,000 g was put thereon so that it was in contact with the cotton, a load was applied thereto, the film was left to stand for 20 minutes, and the amount of increase in weight of a filter paper which was preliminarily put below the porous film was measured to measure the amount of the test liquid which passed and leaked through the porous film. The bleeding amount is preferably smaller than 0.13 g.

(h) Total light transmittance (%): It was measured in accordance with JIS K6718 by means of a Haze meter (model: NDH-200, manufactured by Nippon Denshoku Industries, Co., Ltd.). This value is preferably smaller than 28%.

(i) Film appearance: The uniform drawability of the sample porous film was visually observed and evaluated. Evaluation standards were such that ○: substantially no irregularity by drawing observed, Δ: irregularities by drawing observed, and X: remarkable irregularities by drawing observed.

(j) Masking properties (%): It is a difference between T1 and T2 (T1-T2), wherein T1 and T2 are total light transmittances as measured in accordance with JIS K7105 by means of a Haze meter (model: NDH-200, manufactured by Nippon Denshoku Industries, Co., Ltd.). T1 is a total light transmittance measured in such a manner that one side of a double-faced adhesive tape having a width of 25mm (Kokuyo T-225, tradename, manufactured by Kokuyo Co., Ltd.) was bonded to one surface of the sample porous film, and then the other release paper was peeled off to measure the total light transmittance. T2 is a total light transmittance measured in such a manner that one side of a double-faced adhesive tape having a width of 25 mm (Kokuyo T-225, tradename, manufactured by Kokuyo Co., Ltd.) was bonded to one surface of the sample porous film, the sample was left to stand in constant temperature and high humidity of 40° C. at 75% for 1 week and then recovered to room temperature, and the other release paper was peeled off to measure the total light transmittance. This value is preferably smaller than 30%.

(k) Adhesive strength with time (g/25 mm width): One side of a double-faced adhesive tape having a width of 25 mm (Kokuyo T-225, tradename, manufactured by Kokuyo Co., Ltd.) was bonded to one surface of the porous film to obtain a sample, this sample was left to stand in a constant temperature and constant humidity chamber of 40° C. at 75% for 1 week and then recovered to room temperature, and the other release paper was peeled off and the adhesive tape was bonded to a gauze. The peel stress applied when the adhesive tape and the gauze were peeled off was measured by means of a 180° peeling test in accordance with JIS Z-0237 by using a Tensilon tensile strength tester. The adhesive strength is preferably at least 60 g/25 mm.

Example 1

28.5 Parts by weight of 20 G and 7.0 parts by weight of 441 as the component (A), 61.5 parts by weight of NS#1000 as the component (B) and 3 parts by weight of A as the component (C) were weighed respectively, mixed by a tumbler mixer, and melted and kneaded by means of a tandem kneading extruder having the cylinder temperature set to 220° C. for pelletizing. The obtained pellets were melted by means of an extruder having a T-die attached thereto, with a cylinder temperature set at 200° C., to produce a non-drawn film. This non-drawn film was uniaxially drawn between a roll heated to 60° C. and a drawing roll with a draw ratio of 2.1 times in a drawing direction to obtain a porous film having a thickness of 40 μm. With respect to the obtained porous film, various physical properties were evaluated and the results are shown in Table 1.

Example 2

A porous film was obtained in the same manner as in Example 1 except that 30.0 parts by weight of 20G and 5.0parts by weight of 441 were used as the component (A), Softon 2600 was used as the component (B), B was used as the component (C), and the cylinder temperature was set to 220° C. at the time of pelletizing. With respect to the obtained porous film, various physical properties were evaluated and the results are shown in Table 1.

Example 3

Pelletizing was carried out in the same manner as in Example 1 except that C was used as the component (C), and a porous film was obtained in the same manner as in Example 1. With respect to the obtained porous film, various physical properties were measured and the results are shown in Table 1.

Example 4

Pelletizing was carried out in the same manner as in Example 1 except that a mixture comprising 1.5 parts by weight of A and 1.5 parts by weight of B was used as the component (C), and a porous film was obtained in the same manner as in Example 1. With respect to the obtained porous film, various physical properties were measured and the results are shown in Table 1.

Example 5

Pelletizing was carried out in the same manner as in Example 1 except that D as the component (F) was used instead of the component (C), and a porous film was obtained in the same manner as in Example 1. With respect to the obtained porous film, various physical properties were evaluated and the results are shown in Table 1.

Example 6

Pelletizing was carried out in the same manner as in Example 1 except that E as the component (F) was used instead of the component (C), and a porous film was obtained in the same manner as in Example 1. With respect to the obtained porous film, various physical properties were evaluated and the results are shown in Table 1.

Example 7

Pelletizing was carried out in the same manner as in Example 1 except that F as the component (F) was used instead of the component (C), and a porous film was obtained in the same manner as in Example 1. With respect to the obtained porous film, various physical properties were evaluated and the results are shown in Table 1.

Example 8

Pelletizing was carried out in the same manner as in Example 1 except that G as the component (F) was used instead of the component (C), and a porous film was obtained in the same manner as in Example 1. With respect to the obtained porous film, various physical properties were evaluated and the results are shown in Table 2.

Example 9

Pelletizing was carried out in the same manner as in Example 1. From the obtained pellets, a non-drawn film was produced in the same manner as in Example 1. This non-drawn film was drawn between a roll heated to 60° C. and a drawing roll with a draw ratio of 1.3 times in a drawing direction, then drawn 1.3 times in a direction transverse to the drawing direction by a tenter drawing machine. With respect to the obtained porous film, various physical properties were evaluated and the results are shown in Table 2.

Example 10

Pelletizing was carried out in the same manner as in Example 2. From the obtained pellets, a non-drawn film was produced in the same manner as in Example 2. This non-drawn film was drawn between a roll heated to 60° C. and a drawing roll with a draw ratio of 2.5 times in a drawing direction, then drawn 1.3 times in a direction transverse to the drawing direction by a tenter drawing machine. With respect to the obtained porous film, various physical properties were evaluated and the results are shown in Table 2.

Example 11

Pelletizing was carried out in the same manner as in Example 2. From the obtained pellets, a non-drawn film was produced in the same manner as in Example 2. A porous film was obtained in the same manner as in Example 2 except that the uniaxial draw ratio of the non-drawn film was 5.2 times. With respect to the obtained porous film, various physical properties were evaluated and the results are shown in Table 2.

Example 12

Pelletizing was carried out in the same manner as in Example 2. From the obtained pellets, a non-drawn film was produced in the same manner as in Example 2. A porous film was obtained in the same manner as in Example 2 except that the uniaxial draw ratio of the non-drawn film was 1.1 times. With respect to the obtained porous film, various physical properties were evaluated and the results are shown in Table 2.

Example 13

Pelletizing was carried out in the same manner as in example 2 except that 39.0 parts by weight of 20G, 10.0parts by weight of 411 and 48 parts by weight of Softon 2600 were used, and a porous film was obtained in the same manner as in Example 2. With respect to the obtained porous film, various physical properties were evaluated and the results are shown in Table 2.

Example 14

Pelletizing was carried out in the same manner as in Example 2 except that BF100 was used as the component (B), and a porous film was obtained in the same manner as in Example 2 except that the draw ratio was 1.1 times. With respect to the obtained porous film, various physical properties were evaluated and the results are shown in Table 2.

Example 15

Pelletizing was carried out in the same manner as in Example 2 except that BF100 was used as the component (B), and a porous film was obtained in the same manner as in Example 2. With respect to the obtained porous film, various physical properties were evaluated and the results are shown in Table 2.

TABLE 1

| | Ex. 1 | Ex. 2 | Ex. 3 | Ex. 4 | Ex. 5 | Ex. 6 | Ex. 7 |
|---|---|---|---|---|---|---|---|
| Resin composition components | | | | | | | |
| Component (A) | 20G/441 | 20G/441 | 20G/441 | 20G/441 | 20G/441 | 20G/441 | 20G/441 |
| Amount (parts by weight) | 28.5/7.0 | 30.0/5.0 | 28.5/7.0 | 28.5/7.0 | 28.5/7.0 | 28.5/7.0 | 28.5/7.0 |
| Type of component (B) | NS#1000 | Softon 2600 | NS#1000 | NS#1000 | NS#1000 | NS#1000 | NS#1000 |
| Average particle size (μm) | 1.2 | 0.9 | 1.2 | 1.2 | 1.2 | 1.2 | 1.2 |
| Amount (parts by weight) | 61.5 | 61.5 | 61.5 | 61.5 | 61.5 | 61.5 | 61.5 |
| Type of component (C) | A | B | C | A/B | — | — | — |
| Amount (parts by weight) | 3 | 3 | 3 | 1.5/1.5 | — | — | — |
| Component (F) | — | — | — | — | D | E | F |
| Amount (parts by weight) | — | — | — | — | 3 | 3 | 3 |
| Extrusion conditions | | | | | | | |
| Draw ratio (times) | 2.1 | 2.1 | 2.1 | 2.1 | 2.1 | 2.1 | 2.1 |

TABLE 1-continued

|  | Ex. 1 | Ex. 2 | Ex. 3 | Ex. 4 | Ex. 5 | Ex. 6 | Ex. 7 |
| --- | --- | --- | --- | --- | --- | --- | --- |
| Physical properties of the film |  |  |  |  |  |  |  |
| Thickness (μm) | 40 | 25 | 40 | 40 | 40 | 40 | 40 |
| Heat shrinkage percentage (%) |  |  |  |  |  |  |  |
| MAX | 70 | 66 | 63 | 68 | 69 | 72 | 72 |
| MIN | −19 | −21 | −16 | −17 | −20 | −20 | −18 |
| Maximum pore size (μm) | 0.19 | 0.16 | 0.21 | 0.20 | 0.185 | 0.24 | 0.2 |
| Peak pore size (μm) | 0.13 | 0.10 | 0.14 | 0.14 | 0.12 | 0.14 | 0.15 |
| Porosity (%) | 29 | 32 | 28 | 27 | 32 | 28 | 27 |
| Windability W (sec/100 cc) | 0.8 | 1.15 | 0.9 | 0.8 | 0.86 | 0.9 | 0.87 |
| Gas permeability (sec/50 cc) | 420 | 450 | 450 | 430 | 450 | 460 | 430 |
| Bleeding amount (g) | 0.04 | 0.04 | 0.05 | 0.04 | 0.17 | 0.15 | 0.22 |
| Total light transmittance (%) | 20 | 19 | 21 | 21 | 37 | 29 | 30 |
| Film appearance | ◯ | ◯ | ◯ | ◯ | Δ | Δ | ◯ |
| Masking properties (%) | 22 | 19 | 21 | 21 | 35 | 37 | 30 |

TABLE 2

|  | Ex. 8 | Ex. 9 | Ex. 10 | Ex. 11 | Ex. 12 | Ex. 13 | Ex. 14 | Ex. 15 |
| --- | --- | --- | --- | --- | --- | --- | --- | --- |
| Resin composition components |  |  |  |  |  |  |  |  |
| Component (A) | 20G/411 | 20G/411 | 20G/411 | 20G/411 | 20G/411 | 20G/411 | 20G/411 | 20G/411 |
| Amount (parts by weight) | 28.5/7.0 | 28.5/7.0 | 30.0/5.0 | 30.0/5.0 | 30.0/5.0 | 39.0/10.0 | 30.0/5.0 | 30.0/5.0 |
| Type of component (B) | NS#1000 | NS#1000 | Softon 2600 | Softon 2600 | Softon 2600 | Softon 2600 | BF100 | BF100 |
| Average particle size (μm) | 1.2 | 1.2 | 0.9 | 0.9 | 0.9 | 0.9 | 3.6 | 3.6 |
| Amount (parts by weight) | 61.5 | 61.5 | 61.5 | 61.5 | 61.5 | 48.0 | 61.5 | 61.5 |
| Type of component (C) | — | A | B | B | B | B | B | B |
| Amount (parts by weight) | — | 3 | 3 | 3 | 3 | 3 | 3 | 3 |
| Component (F) | G | — | — | — | — | — | — | — |
| Amount (parts by weight) | 3 | — | — | — | — | — | — | — |
| Extrusion conditions |  |  |  |  |  |  |  |  |
| Draw ratio (times) | 2.1 | 1.3 × 1.3 Biaxial Orientation | 2.5 × 1.3 Biaxial Orientation | 5.2 | 1.1 | 2.1 | 1.1 | 2.1 |
| Physical properties of the film |  |  |  |  |  |  |  |  |
| Thickness (μm) | 40 | 40 | 40 | 40 | 40 | 40 | 40 | 40 |
| Heat shrinkage percentage (%) |  |  |  |  |  |  |  |  |
| MAX | 68 | 32 | 65 | 100 | 25 | 68 | 32 | 71 |
| MIN | −16 | 20 | 5 | −30 | −2 | −20 | −2 | −19 |
| Maximum pore size (μm) | 0.23 | 0.31 | 0.36 | 0.25 | 0.04 | 0.21 | 0.35 | 0.42 |

TABLE 2-continued

|  | Ex. 8 | Ex. 9 | Ex. 10 | Ex. 11 | Ex. 12 | Ex. 13 | Ex. 14 | Ex. 15 |
|---|---|---|---|---|---|---|---|---|
| Peak pore size (μm) | 0.17 | 0.22 | 0.20 | 0.20 | 0.03 | 0.17 | 0.30 | 0.42 |
| Porosity (%) | 27 | 12 | 41 | 43 | 9 | 30 | 9 | 33 |
| Windability W (sec/100 cc) | 0.96 | 0.39 | 0.41 | 1.1 | 0.38 | 6.4 | 0.57 | 0.14 |
| Gas permeability (sec/50 cc) | 420 | 300 | 100 | 250 | 2900 | 2500 | 420 | 20 |
| Bleeding amount (g) | 0.27 | 0.21 | 0.35 | 0.17 | 0.02 | 0.04 | 0.25 | 0.55 |
| Total light transmittance (%) | 30 | 35 | 18 | 15 | 38 | 38 | 35 | 21 |
| Film appearance | X | ◯ | ◯ | Δ | ◯ | ◯ | ◯ | Δ |
| Masking properties (%) | 35 | 21 | 35 | 36 | 21 | 21 | 25 | 35 |

The following was found from Tables 1 and 2.

(1) A porous film containing the components (A), (B) and (C) and having a shrinkage percentage as defined in claim 1 (the film shrinks by from 40 to 95% in one direction and expands by from 5 to 40% in a direction transverse thereto) is excellent in gas permeability, anti-bleeding properties, hiding properties and masking properties at an adhesion portion (Examples 1 to 4).

(2) On the contrary, a porous film containing the components (A) and (B) but containing no component (C), is poor in anti-bleeding properties, hiding properties and masking properties at an adhesion portion (Examples 5to 8).

(3) A biaxially orientated film does not satisfy the shrinkage percentage as defined in claim 1 even if the draw ratio is low, has a maximum pore size and a windability W out of the preferred ranges, and is poor in e.g. anti-bleeding properties and hiding properties (Example 9).

(4) A biaxially oriented film having a high draw ratio does not satisfy the shrinkage percentage as defined in claim 1, has a maximum pore size out of the preferred range, and is poor in e.g. anti-bleeding properties and masking properties at an adhesion portion (Example 10).

(5) A film having a uniaxial draw ratio higher than the preferred range does not satisfy the shrinkage percentage as defined in claim 1, has a porosity out of the preferred range, and is poor in e.g. anti-bleeding properties and masking properties at an adhesion portion (Example 11).

(6) A film having a uniaxial draw ratio lower than the preferred range does not satisfy the shrinkage percentage as defined in claim 1, has a maximum pore size and a porosity out of the preferred ranges, and has a low gas permeability, such being unfavorable (Example 12).

(7) In a case where the blending amount of the component (B) relative to the component (A) is small, a porous film having a windability W out of the preferred range is obtained, and the gas permeability tends to be low, such being unfavorable (Example 13).

(8) A film obtained by blending a bulking agent having an average particle size larger than the range as defined in claim 3 (from 0.5 to 3.0 μm), followed by uniaxial drawing with a draw ratio lower than the preferred range, does not satisfy the shrinkage percentage as defined above in claim 1, has a porosity and a maximum pore size out of the preferred ranges, and is poor in anti-bleeding properties (Example 14).

(9) A film obtained by blending a bulking agent having an average particle size larger than the range as defined in claim 3, followed by uniaxial drawing with a draw ratio within the preferred range, satisfies the shrinkage percentage as defined in claim 1, but has an extremely high gas permeability, and the bleeding amount is large, such being unfavorable (Example 15).

Examples 16 to 27

Materials Used Other Than the Above-Described Components (1) HC-WX: Hardened castor oil as the component (D) (Castorwax HC-WX, tradename, manufactured by HOKOKU Corporation).
(2) DCO: Dehydrated castor oil as the component (D) (DCO, tradename, manufactured by HOKOKU Corporation).
(3) TSF451-3000: Silicone oil as the component (C) (Dimethylsilicone TSF451-3000, tradename, manufactured by GE Toshiba Silicones Co., Ltd.).
(4) HIVAC F-5: Silicone oil as the component (C) (Methylphenylsilicone oil HIVAC F-5, tradename, manufactured by Shin-Etsu Silicone K.K.)
(5) KF861: Silicone oil as the component (C) (Amino-modified silicone oil KF-861, tradename, manufactured by Shin-Etsu Silicone K.K.).
(6) B3000: Polybutadiene as the component (F) (B3000, tradename, manufactured by NIPPON SODA Co., Ltd.).
(7) J-4081: Tetraglycerol stearate as the component (F) (POEM J-4081, tradename, manufactured by Riken Vitamin Co., Ltd.).
(8) S-95: Glycerol tri-distearate as the component (F) (POEM S-95, tradename, manufactured by Riken Vitamin Co., Ltd.).

Example 16

30.0 Parts by weight of 20G and 5.0 parts by weight of 441 as the component (A), 63.0 parts by weight of NS#1000 having an average particle size of 1.2 μm, 2parts by weight of HC-WX and 2 parts by weight of TFS451-3000 were weighed respectively, mixed by a tumbler mixer, and then melted and kneaded by means of a tandem kneading extruder having the cylinder temperature set to 220° C. for pelletizing. The obtained pellets were melted by means of an extruder having a T-die attached thereto, with a cylinder temperature set to 200° C., to produce a non-drawn film. The obtained non-drawn film was uniaxially drawn between a roll heated to 60° C. and a drawing role with a draw ratio of 2.0 times in a drawing direction to obtain a porous film having a thickness of 25 μm. With respect to the obtained porous film, various physical properties were evaluated and the results are shown in Table 3.

Example 17

A porous film was obtained in the same manner as in Example 16 except that 28.5 parts by weight of 20G and 7.0 parts by weight of 441 were used as the component (A), 3 parts by weight of HIVACF-5 was used as the component (C), and 1.5 parts by weight of DCO was used as the component (D). With respect to the obtained porous film, various physical properties were measured and the results are shown in Table 3.

Example 18

A porous film was obtained in the same manner as in Example 16 except that KF861 was used as the component (C), and 3 parts by weight of HC-WX was used as the component (D). With respect to the obtained porous film, various physical properties were measured and the results are shown in Table 3.

Example 19

Pelletizing was carried out in the same manner as in Example 17 except that 4.5 parts by weight of HC-WX as a component (D) was used without component (C), and a porous film was obtained in the same manner as in Example 17. With respect to the obtained porous film, various physical properties were evaluated and the results are shown in Table 3.

Example 20

Pelletizing was carried out in the same manner as in Example 16 except that a mixture comprising 2 parts by weight of HC-WX as the component (D) and 4 parts by weight of B-3000 as the component (F) was used without component (C), and a porous film was obtained in the same manner as in Example 16. With respect to the obtained porous film, various physical properties were evaluated and the results are shown in Table 3.

Example 21

Pelletizing was carried out in the same manner as in Example 16 except that a mixture comprising 2 parts by weight of HC-WX as the component (D) and 2 parts by weight of J-4081 as the component (F) was used without component (C), and a porous film was obtained in the same manner as in Example 16. With respect to the obtained porous film, various physical properties were evaluated and the results are shown in Table 4.

Example 22

Pelletizing was carried out in the same manner as in Example 17, and from the obtained pellets, a non-drawn film was produced in the same manner as in Example 17. The obtained non-drawn film was drawn between a roll heated to 60° C. and a drawing roll with a draw ratio of 1.3 times in a drawing direction, and then drawn 1.2 times in a direction transverse to the drawing direction by a tenter drawing machine. With respect to the obtained porous film, various physical properties were evaluated and the results are shown in Table 4.

Example 23

A porous film was obtained in the same manner as in Example 16 except that the draw ratio was 5.2. With respect to the obtained porous film, various physical properties were evaluated and the results are shown in Table 4.

Example 24

A porous film was obtained in the same manner as in Example 16 except that the draw ratio was 1.1. With respect to the obtained porous film, various physical properties were evaluated and the results are shown in Table 4.

Example 25

A porous film was obtained in the same manner as in Example 24 except that calcium carbonate having an average particle size of 3.6 μm was used as the component (B). With respect to the obtained porous film, various physical properties were evaluated and the results are shown in Table 4.

Example 26

A porous film was obtained in the same manner as in Example 25 except that the draw ratio was 2.0. With respect to the obtained porous film, various physical properties were evaluated and the results are shown in Table 4.

TABLE 3

|  | Ex. 16 | Ex. 17 | Ex. 18 | Ex. 19 | Ex. 20 |
|---|---|---|---|---|---|
| Resin composition |  |  |  |  |  |
| Type of component (A) | 20G/441 | 20G/441 | 20G/441 | 20G/441 | 20G/441 |
| Amount (parts by weight) | 30/5 | 28.5/7 | 30/5 | 28.5/7 | 30/5 |
| Type of component (B) | NS#1000 | NS#1000 | NS#1000 | NS#1000 | NS#1000 |
| Average particle size (μm) | 1.2 | 1.2 | 1.2 | 1.2 | 1.2 |
| Amount (parts by weight) | 63 | 63 | 63 | 63 | 63 |
| Type of component (C) | TFS451-3000 | HIVACF-5 | KF861 | — | — |
| Amount (parts by weight) | 2 | 3 | 3 | — | — |

TABLE 3-continued

|  | Ex. 16 | Ex. 17 | Ex. 18 | Ex. 19 | Ex. 20 |
| --- | --- | --- | --- | --- | --- |
| Type of component (D) | HC-WX | DCO | HC-WX | HC-WX | HC-WX |
| Amount (parts by weight) | 2 | 1.5 | 3 | 4.5 | 2 |
| Type of component (F) | — | — | — | — | B-3000 |
| Amount (parts by weight) | — | — | — | — | 4 |
| Extrusion conditions |  |  |  |  |  |
| Draw ratio (times) | 2.0 | 2.0 | 2.0 | 2.0 | 2.0 |
| Physical properties of the film |  |  |  |  |  |
| Thickness (μm) | 25 | 40 | 25 | 40 | 25 |
| Heat shrinkage percentage (%) |  |  |  |  |  |
| MAX | — | 70 | — | — | — |
| MIN | — | 20 | — | — | — |
| Maximum pore size (μm) | 0.18 | 0.17 | 0.19 | 0.185 | 0.23 |
| Peak pore size (μm) | 0.08 | 0.14 | 0.10 | 0.11 | 0.09 |
| Porosity (%) | 30 | 29 | 27 | 32 | 28 |
| Windability W (sec/100 cc) | 0.8 | 1 | 1 | 0.86 | 0.9 |
| Gas permeability (sec/50 cc) | 420 | 500 | 450 | 470 | 450 |
| Bleeding amount (g) | 0.05 | 0.04 | 0.07 | 0.13 | 0.17 |
| Total light transmittance (%) | 25 | 22 | 27 | 35 | 37 |
| Film appearance | ○ | ○ | ○ | Δ | Δ |
| Adhesive strength with time (g/25 mm width) | 90 | 70 | 110 | 120 | 50 |
| masking properties (%) | 11 | 12 | 6 | 4.5 | 31 |

TABLE 4

|  | Ex. 21 | Ex. 22 | Ex. 23 | Ex. 24 | Ex. 25 | Ex. 26 |
| --- | --- | --- | --- | --- | --- | --- |
| Resin composition |  |  |  |  |  |  |
| Type of component (A) | 20G/441 | 20G/441 | 20G/441 | 20G/441 | 20G/441 | 20G/441 |
| Amount (parts by weight) | 30/5 | 30/5 | 30/5 | 30/5 | 30/5 | 30/5 |
| Type of component (B) | NS#1000 | NS#1000 | NS#1000 | NS#1000 | NS#1000 | NS#1000 |
| Average particle size (μm) | 1.2 | 1.2 | 1.2 | 1.2 | 3.6 | 3.6 |
| Amount (parts by weight) | 63 | 63 | 63 | 63 | 63 | 63 |
| Type of component (C) | — | HIVACF-5 | TFS451-3000 | TFS451-3000 | TFS451-3000 | TFS451-3000 |
| Amount (parts by weight) | — | 3 | 2 | 2 | 2 | 2 |
| Type of component (D) | HC-WX | DCO | HC-WX | HC-WX | HC-WX | HC-WX |
| Amount (parts by weight) | 2 | 1.5 | 2 | 2 | 2 | 2 |
| Type of component (F) | J-4081 | — | — | — | — | — |
| Amount (parts by weight) | 2 | — | — | — | — | — |
| Extrusion conditions |  |  |  |  |  |  |
| Draw ratio (times) | 2.0 | 1.3 × 1.2 Biaxial Orientation | 5.2 | 1.1 | 1.1 | 2.0 |

TABLE 4-continued

|  | Ex. 21 | Ex. 22 | Ex. 23 | Ex. 24 | Ex. 25 | Ex. 26 |
|---|---|---|---|---|---|---|
| Physical properties of the film | | | | | | |
| Thickness (μm) | 25 | 40 | 40 | 40 | 40 | 40 |
| Heat Shrinkage percentage (%) | | | | | | |
| MAX | — | 35 | 102 | 30 | 29 | 69 |
| MIN | — | 19 | −35 | −2 | −1 | −21 |
| Maximum pore size (μm) | 0.2 | 0.31 | 0.29 | 0.03 | 0.32 | 0.38 |
| Peak pore size (μm) | 0.09 | 0.27 | 0.24 | 0.02 | 0.20 | 0.38 |
| Porosity (%) | 33 | 15 | 41 | 8 | 9 | 29 |
| Windability W (sec/100 cc) | 1.2 | 0.7 | 1.2 | 0.3 | 0.45 | 0.22 |
| Gas permeability (sec/50 cc) | 500 | 350 | 244 | 3700 | 500 | 40 |
| Bleeding amount (g) | 0.09 | 0.17 | 0.14 | 0.03 | 0.14 | 0.3 |
| Total light transmittance (%) | 30 | 32 | 18 | 38 | 40 | 25 |
| Film appearance | ○ | ○ | ○ | ○ | ○ | ○ |
| Adhesive strength with time (g/25 mm width) | 20 | 50 | 30 | 120 | 70 | 20 |
| Masking properties (%) | 20 | 18 | 28 | 10 | 10 | 25 |

From Tables 3 and 4, the following was found.

(1) A porous film containing the components (A), (B), (C) and (D) and having a shrinkage percentage as defined in claim 1 (the film shrinks by from 40 to 95% in one direction and expands by from 5 to 40% in a direction transverse thereto) is excellent in e.g. gas permeability, anti-bleeding properties, hiding properties and masking properties at an adhesion portion (Examples 16 to 18).

(2) A film containing the components (A) and (B), containing a large amount of the component (D) alone and containing no component (C) is poor in hiding properties only or hiding properties and appearance (Examples 19 to 21).

(3) A biaxially oriented film does not satisfy the shrinkage percentage as defined in claim 1 even if the draw ratio is low, has a maximum pore size out of the preferred range, and with which the bleeding amount is large (Example 22).

(4) A film containing the components (A), (B), (C) and (D), but having a draw ratio larger than the preferred range, has a heat shrinkage percentage out of the preferred range, a porosity larger than the preferred range, and is extremely poor in adhesive strength with time (Example 23).

(5) A film containing the components (A), (B), (C) and (D), but having a draw ratio lower than the preferred range, has a heat shrinkage percentage out of the preferred range, and a porosity and a windability W smaller than the preferred ranges, and is thereby poor in gas permeability (Example 24).

(6) A film containing as the component (B) one having an average particle size larger than the range as defined in claim 3 (from 0.5 to 3.0 μm), obtained by drawing with a draw ratio lower than the preferred range, has a heat shrinkage percentage out of the preferred range, has a low porosity, and is poor in anti-bleeding properties and hiding properties (Example 25).

(7) A film containing as the component (B) one having an average particle size larger than the range as defined in claim 3, obtained by drawing with a preferred draw ratio, has an extremely high gas permeability, such being unfavorable (Example 26).

INDUSTRIAL APPLICABILITY

According to the present invention as explained above in detail, the following preferable effects are obtained, and the present invention is highly useful industrially.

1) The porous film of the present invention is a porous film excellent in anti-bleeding properties, gas permeability, adhesive properties, masking properties and hiding properties.

2) The porous film of the present invention is Excellent in anti-bleeding properties, gas permeability, adhesive properties, masking properties and hiding properties, is less likely to be transparent due to bleeding of an adhesive at an adhesion portion with an underwear or another component, and has high hiding properties in appearance also, whereby urine or blood is less likely to leak therethrough, and accordingly the porous film of the present invention is useful as a moisture permeable back sheet covering a moisture (water) absorptive material for e.g. paper diapers or napkins.

3) According to the process for producing a porous film of the present invention, a porous film excellent in moisture permeability, anti-bleeding properties, hiding properties and masking properties at an adhesion portion can be stably produced.

The invention claimed is:

1. A porous film obtained by melting and kneading a resin composition consisting of a polyolefin resin {component (A)} and a bulking agent {component (B)} as the main components, and a silicone {component (C)} and a castor oil {component (D)}, followed by drawing, which shrinks by from 40 to 95% in one direction and expands by from 5 to 40% in a direction transverse thereto, when soaked in a first silicone oil of 200° C. for 60 seconds, wherein the castor oil and the silicone are present in a weight ratio of from 0.5 to 1.0 and the castor oil and the silicone are uniformly dispersed within the polyolefin, wherein the drawing is a uniaxial drawing in only one direction to a total draw ratio of from 1.2 to 5.0 at a temperature of from 23° C. to the softening temperature of the resin as measured in accordance with JIS K6760, wherein the silicone is at least one selected from the group consisting of a polysiloxane and a silicone rubber, and wherein the castor oil consists of the hardened castor oil.

2. The porous film according to claim 1, wherein the silicone is present in an amount of from 0.1 to 10 parts by weight of the components (A) and (B), wherein component (A) is present in an amount of from 25 to 50 parts by weight of a polyolefin resin and component (B) is present in an amount of from 75 to 50 parts by weight of an inorganic bulking agent.

3. The porous film according to claim 2, wherein the polyolefin resin {component (A)} is a mixture of from 30 to 98 wt % of a linear low density polyethylene having a melt index of from 0.1 to 8 g/10 mm in accordance with JIS K7210 and a density of from 0.890 to 0.950 g/cm$^3$, and from 2 to 70 wt % of a branched low density polyethylene having a melt index of from 0.1 to 8 g/10 mm and a density of from 0.900 to 0.930 g/cm$^3$.

4. The porous film according to claim 2, which has a maximum pore size of from 0.05 to 0.3 μm, a porosity of from 10 to 40%, and a windability W of from 0.4 to 4.0.

5. The porous film according to claim 2, which has a thickness of from 10 to 200 μm.

6. A back sheet for a disposable sanitary napkin, which comprises the porous film as defined in claim 2.

7. A back sheet for a disposable diaper, which comprises the porous film as defined in claim 2.

8. The porous film according to claim 1, wherein a mixture {component (E)} comprising the component (C) and the component (D) is present in an amount of from 0.1 to 10 parts by weight; the component (A) is present in an amount of from 25 to 50 parts by weight of a polyolefin resin; and the component B is present in an amount of from 75 to 50 parts by weight of an inorganic bulking agent based on 100 parts by weight of the components (A) and (B), and wherein component (B) has an average particle size of from 0.5 to 3.0 μm.

9. The porous film according to claim 8, wherein the polyolefin resin {component (A)} is a mixture of from 30 to 98 wt % of a linear low density polyethylene having a melt index of from 0.1 to 8 g/10 mm (in accordance with JIS K7210) and a density of from 0.890 to 0.950 g/cm$^3$, and from 2 to 70 wt % of a branched low density polyethylene having a melt index of from 0.10 to 8 g/10 mm and a density of from 0.900 to 0.930 g/cm$^3$.

10. The porous film according to claim 8, which has a maximum pore size of from 0.05 to 0.3 μm, a porosity of from 10 to 40%, and a windability W of from 0.4 to 4.0.

11. The porous film according to claim 8, which has a thickness of from 10 to 200 μm.

12. A back sheet for a disposable sanitary napkin, which comprises the porous film as defined in claim 8.

13. A back sheet for a disposable diaper, which comprises the porous film as defined in claim 8.

14. The porous film according to claim 1, wherein the polyolefin resin {component (A)} is a mixture comprising from 30 to 98 wt % of a linear low density polyethylene having a melt index of from 0.1 to 8 g/10 min (in accordance with JIS K7210) and a density of from 0.890 to 0.950 g/cm$^3$, and from 2 to 70 wt % of a branched low density polyethylene having a melt index of from 0.1 to 8 g/10 min and a density of from 0.900 to 0.930 g/cm$^3$.

15. The porous film according to claim 1, wherein the silicone oil is dimethyl polysiloxane (dimethylsilicone).

16. The porous film according to claim 1, which has a maximum pore size of from 0.05 to 0.3 μm, a porosity of from 10 to 40%, and a windability W of from 0.4 to 4.0.

17. The porous film according to claim 1, which has a thickness of from 10 to 200 μm.

18. A back sheet for a disposable sanitary napkin, which comprises the porous film as defined in claim 1.

19. A back sheet for a disposable diaper, which comprises the porous film as defined in claim 1.

20. The porous film of claim 1, wherein the polyolefin resin and the silicone are mixed to form a preliminary mixture which is then mixed with the bulking agent prior to the melting and kneading.

* * * * *